(12) United States Patent
Svensson et al.

(10) Patent No.: US 9,301,932 B2
(45) Date of Patent: Apr. 5, 2016

(54) LIQUID PHARMACEUTICAL COMPOSITION COMPRISING NITISINONE

(75) Inventors: Lennart Svensson, Solna (SE); Hans Sidén, Sollentuna (SE)

(73) Assignee: SWEDISH ORPHAN BIOVITRUM INTERNATIONAL AB, Stockholm (SE)

( * ) Notice: Subject to any disclaimer, the term of this patent is extended or adjusted under 35 U.S.C. 154(b) by 253 days.

(21) Appl. No.: 14/129,090

(22) PCT Filed: Jun. 20, 2012

(86) PCT No.: PCT/SE2012/050681
§ 371 (c)(1),
(2), (4) Date: Mar. 27, 2014

(87) PCT Pub. No.: WO2012/177214
PCT Pub. Date: Dec. 27, 2012

(65) Prior Publication Data
US 2014/0206771 A1    Jul. 24, 2014

(30) Foreign Application Priority Data
Jun. 23, 2011 (SE) .................................. 1150585

(51) Int. Cl.
| A61K 31/122 | (2006.01) |
|---|---|
| A61K 47/12 | (2006.01) |
| A61K 47/10 | (2006.01) |
| A61K 47/26 | (2006.01) |
| A61K 9/10 | (2006.01) |
| A61K 47/38 | (2006.01) |

(52) U.S. Cl.
CPC ............. *A61K 31/122* (2013.01); *A61K 9/10* (2013.01); *A61K 47/10* (2013.01); *A61K 47/12* (2013.01); *A61K 47/26* (2013.01); *A61K 47/38* (2013.01)

(58) Field of Classification Search
CPC .................. A61K 31/122; A61K 47/12
See application file for complete search history.

(56) References Cited

U.S. PATENT DOCUMENTS

| 4,695,673 A | 9/1987 | Heather et al. |
|---|---|---|
| 5,006,158 A | 4/1991 | Carter et al. |
| 5,550,165 A | 8/1996 | Ellis et al. |
| 5,668,089 A | 9/1997 | Shribbs et al. |
| 2005/0288187 A1 | 12/2005 | Hanauske-Abel et al. |
| 2010/0227936 A1 | 9/2010 | Moran et al. |

FOREIGN PATENT DOCUMENTS

| JP | 2007-529440 | 10/2007 |
|---|---|---|
| JP | 2008-504354 | 2/2008 |
| WO | WO-2005/089548 | 9/2005 |
| WO | WO-2006/003371 | 1/2006 |
| WO | WO-2006/090177 | 8/2006 |
| WO | WO-2008/020150 | 2/2008 |
| WO | WO-2010/054273 | 5/2010 |
| WO | WO-2013/181292 | 12/2013 |

OTHER PUBLICATIONS

Introne et al. Molecular Genetics and Metabolism, Aug. 2011, vol. 103, pp. 307-314 (Published Online May 6, 2011).*
Hu, "Cyclohexanedione Herbicide Sulcotrione Research," Chinese Doctoral Dissertations & Master's Theses Full-text Database (Master), Engineering Science and Technology I, No. 2, pp. 16, 17 and 23 (Dec. 15, 2002).
Endo et al., "Tyrosinemia" Japanese Journal of Clinical Medicine (suppl.), 34th Series of syndromes by regions, congenital syndromes-dictionary-[*in Japanese*] (last volume) (translation included), Jul. 28, 2001, p. 773-775.
Fieser L.F. and Fieser M. (eds.), Reagents for Organic Synthesis, J. Wiley and Sons, New York (1967) vol. 1, pp. 767-769.
Hall et al., "Pharmacokinetics and pharmacodynamics of NTBC (2-(2-nitro-4- fluoromethylbenzoyl)-1,3-cyclohexanedione) and mesotrione, inhibitors of 4-hydroxyphenyl pyruvate dioxygenase (HPPD) following a single dose to healthy male volunteers," Br. J. Clin. Pharmacol. (2001) 52(2):169-177.
Haupstein et al., "Trifluoromethyl Derivatives of Hydroxybenzoic Acids and Related Compounds," J. Am. Chem. Soc. (1954) 76(4), 1051-1054.
International Preliminary Report on Patentability and Written Opinion for PCT/SE2012/050681, dated Dec. 23, 2013, 6 pages.
International Search Report for PCT/SE2012/050681, mailed Sep. 4, 2012, 4 pages.
Suwannarat et al., "Use of nitisinone in patients with alkaptonuria," Metab., Clin. Exp. (2005) 54(6):719-728.

* cited by examiner

*Primary Examiner* — James D Anderson
(74) *Attorney, Agent, or Firm* — Morrison & Foerster LLP

(57) ABSTRACT

The invention concerns a liquid pharmaceutical formulation suitable for oral administration, comprising a suspension of an effective amount of micronized 2-(2-nitro-4-trifluoromethylbenzoyl)-1,3-cyclohexanedione (nitisinone); and citric acid buffer having a pH in the range of 2.5 to 3.5. The formulation is useful in the treatment of disorders and diseases in which inhibition of 4-hydroxyphenylpyruvate dioxygenase (HPPD) is desirable, e.g. in hereditary tyrosinaemia type I.

25 Claims, No Drawings

LIQUID PHARMACEUTICAL COMPOSITION COMPRISING NITISINONE

CROSS REFERENCE TO RELATED APPLICATIONS

This application is a U.S. National Phase Application of International Application No. PCT/SE2012/050681, filed Jun. 20, 2012, which claims priority to and the benefit of Swedish Patent Application No. 1150585-6, filed on Jun. 23, 2011, the entire contents of each of which are incorporated herein by reference in their entireties.

TECHNICAL FIELD

This invention concerns pharmaceutical formulations comprising 2-(2-nitro-4-trifluoromethylbenzoyl)-1,3-cyclohexanedione (nitisinone) as an active agent. The formulations are useful in the treatment of disorders and diseases in which inhibition of 4-hydroxyphenylpyruvate dioxygenase (HPPD) is desirable, e.g. in hereditary tyrosinaemia type I.

BACKGROUND ART

The compound 2-(2-nitro-4-trifluoromethylbenzoyl)-1,3-cyclohexanedione, also known as nitisinone or NTBC, was first disclosed as a herbicide (U.S. Pat. No. 5,006,158; U.S. Pat. No. 4,695,673; U.S. Pat. No. 5,668,089).

Nitisinone is used under the brand name Orfadin® for the treatment of hereditary tyrosinemia type I (HT-1), a rare paediatric disease. HT-1 is a genetic metabolic disorder that results from an inability to break down the amino acid tyrosine. Because of resulting liver failure and liver cancer, children with HT-1 rarely survive into their twenties without a liver transplant.

As disclosed in e.g. U.S. Pat. No. 5,550,165, nitisinone is a competitive inhibitor of 4-hydroxyphenyl-pyruvate dioxygenase (HPPD), an enzyme upstream of fumarylacetoacetate hydrolase (FAH) in the tyrosine catabolic pathway. By inhibiting the normal catabolism of tyrosine in patients with HT-1, nitisinone prevents the accumulation of the catabolic intermediates maleylacetoacetate and fumarylacetoacetate. In patients with HT-1, these catabolic intermediates are converted to the toxic metabolites succinylacetone and succinylacetoacetate, which are responsible for the observed liver and kidney toxicity.

Further, nitisinone has been described as being useful in the treatment of other disorders, such as Parkinson's disease (WO 2006/090117); depression (WO 2008/020150); restless leg syndrome (WO 2010/054273); and alkaptonuria (Sunwanarat, P. et al., Metabolism 54: 719-728, 2005). The use of nitisinone has also been disclosed in a method for enhancing phagolysosomal fusion following infection of a patient with a microorganism (U.S. patent application, publication No. 2010-0227936).

Oral administration of drugs is one of the preferred routes for treatment, because of its simplicity. While drugs are generally administered in the form of tablets or capsules, such administration may be less preferred, for example when the dosage has to be finely adapted to treated subject, or may be less convenient, for example in the case of paediatric or veterinary drugs. The liquid dosage form may then be an advantageous alternative.

Consequently, there is a need for stable liquid nitisinone compositions which are adapted for administration to paediatric patients and overcome the drawbacks with solid pharmaceutical compositions.

DISCLOSURE OF THE INVENTION

According to the invention it has been shown that liquid pharmaceutical formulation, comprising a suspension of micronized nitisinone, and having a pH of about 3, has surprisingly advantageous properties such as increased stability. Consequently, the present invention relates to a liquid pharmaceutical formulation suitable for oral administration, comprising (a) a suspension of an effective amount of micronized 2-(2-nitro-4-trifluoromethylbenzoyl)-1,3-cyclohexanedione (nitisinone); and (b) citric acid buffer having a pH in the range of 2.5 to 3.5, preferably pH 3.0.

The term "effective amount" of nitisinone should be understood as an amount effective to inhibit 4-hydroxyphenypyruvate dioxygenase. Preferably, the amount of nitisinone is 1 to 10 mg/ml, more preferably 4 mg/ml.

Nitisinone may be obtained by conventional procedures of organic chemistry already known for the production of structurally analogous materials. Thus, for example, nitisinone may be conveniently obtained by reaction of 2-nitro-4-trifluoromethylbenzoyl chloride with cyclohexane-1,3-dione in the presence of acetone cyanhydrin and a suitable base such as triethylamine, as disclosed in U.S. Pat. No. 5,550,165. The starting 2-nitro-4-trifluoromethylbenzoyl chloride may itself be obtained from the corresponding benzoic acid, for example by reaction with thionyl chloride or oxalyl chloride as is described in Reagents for Organic Synthesis, (J Wiley and Sons, 1967; Vol. 1, pp. 767-769) and is generally used without special purification. Similarly, 2-nitro-4-trifluoromethylbenzoic acid may be obtained, for example, as described by Haupstein et al. in J. Amer. Chem. Soc., 1954, 76, 1051, or by one of the general methods described in The Chemistry of Carboxylic Acids and Esters (J Wiley and Sons, 1969; editor: S. Patai) and Survey of Organic Synthesis (J Wiley and Sons, 1970; C. A. Buehler and D. F. Pearson).

Preferably, the formulation according to the invention in addition comprises one or more pharmaceutically acceptable constituents selected from the group consisting of suspending agents, sweeteners, preservatives, surfactants, and flavoring agents.

A suitable suspending agent is e.g. hydroxypropyl methylcellulose (HPMC) in an amount of 1 to 20 mg/ml, preferably 5 mg/ml.

A suitable sweetener is glycerol, in an amount which results in an acceptable taste. The amount of glycerol is preferably 100 to 500 mg/ml, more preferably 500 mg/ml.

The formulation according to the invention preferably comprises at least one preservative chosen from methyl paraben, propyl paraben and sodium benzoate. Preferably, the preservatives are methyl paraben in an amount of 1 to 2 mg/ml, more preferably 1.4 mg/ml; propyl paraben in an amount of 0.1 to 0.2 mg/ml, more preferably 0.14 mg/ml; and sodium benzoate in an amount of 0.2 to 5 mg/ml, more preferably 1.0 mg/ml.

The formulation according to the invention preferably comprises a surfactant, such as polysorbate 80 (polyoxyethylene (80) sorbitan monooleate; common commercial brand names include Alkest TW 80™ and Tween 80™). The amount of polysorbate 80 should be sufficient to wet nitisinone particles to facilitate the dispersion of nitisinone during manufacturing, as well as to avoid any agglomeration of the nitisinone particles during storage of the final product. Preferably the formulation according to the invention comprises Polysorbate 80 in an amount of 0.1 to 20 mg/ml, more preferably from 0.10 to 0.15 mg/ml, such as about 0.135 mg/ml.

The formulation according to the invention preferably comprises an aroma agent, such as strawberry flavor. The amount of flavor should be sufficient to achieve an acceptable taste of the formulation and preferably in an amount of 0.2 to 1.1 mg/ml, more preferably 0.7 mg/ml.

In an especially preferred form, the formulation according to the invention comprises
(a) nitisinone (4 mg/ml);
(b) citric acid monohydrate (9 mg/ml);
(c) trisodium citrate dehydrate (2.1 mg/ml)
(d) hydroxypropyl methylcellulose (5 mg/ml);
(e) glycerol (500 mg/ml);
(f) methyl paraben (1.4 mg/ml);
(g) propyl paraben (0.14 mg/ml); and
(h) polysorbate 80 (0.14 mg/ml).

In another especially preferred form, the formulation according to the invention comprises
(a) nitisinone (4 mg/ml);
(b) citric acid monohydrate (9 mg/ml);
(c) trisodium citrate dehydrate (2.1 mg/ml)
(d) hydroxypropyl methylcellulose (5 mg/ml);
(e) glycerol (500 mg/ml);
(f) sodium benzoate (1.0 mg/ml); and
(g) polysorbate 80 (0.14 mg/ml).

A further preferred form of the formulation comprises a flavoring agent such as: (h) strawberry flavor (0.7 mg/ml).

The formulation according to the invention is useful for the treatment of medical disorders and diseases wherein inhibition of 4-hydroxyphenyl-pyruvate dioxygenase (HPPD) is desirable. Examples of such conditions include hereditary tyrosinaemia type 1 (HT-1), Parkinson's disease, depression, restless leg syndrome and alkaptonuria.

The formulation according to the invention is particularly useful for paediatric use. Specifically, is it suitable for newborn infants up to children 8-10 years of age, representing a body weight span of approximately 3.5 to 40 kg. A daily dose of 1 mg/kg thus corresponds to a dose range from 2×1.75 mg to 2×20 mg. A strength of 4 mg/ml will achieve acceptable dosage volumes corresponding 0.44 to 5 ml administered twice daily. An oral syringe is suitable as administration dispenser for accurate dosing in this range.

EXAMPLES

Example 1

Micronization of Nitisinone

A lab-scale air-jet mill, 2 inches qualification model, Sturtevant Inc., was used to micronize nitisinone obtained from the company Bachem, Switzerland. The mill was operated with tangential flow (i.e. the air and drug are fed in the same direction in the milling chamber). The unmilled drug was fed into the mill using a Venturi feed system, Syncron®, Magnet Feeder model F-TO-C, where air was used to draw the feed material into the milling chamber. A product filter bag was affixed to the outlet of the mill, through which the exhausts and the milled drug collects. The milling conditions were set as follows:
Grind air: Dry nitrogen gas
Grind pressure: 90 psi
Feed pressure: 85 psi
Room conditions: Ambient
5 g of the API was passed through the lab-scale micronizer and the resulting material was collected (3.7 g). The material was analyzed for/by particle size diameter (PSD), assay and purity by high performance liquid chromatography (HPLC), x-ray powder diffraction (XRPD), differential scanning calorimetry (DSC) and polarized light microscopy (PLM). The results for PSD from the micronization are shown in Table I.

TABLE I

| | Particle size diameter (microns) | | | | |
| --- | --- | --- | --- | --- | --- |
| | $d_{10}$ | $d_{20}$ | $d_{50}$ | $d_{80}$ | $d_{90}$ |
| Start material | 20.50 | 33.10 | 60.01 | 94.42 | 115.11 |
| Micronized material | 0.30 | 0.47 | 1.29 | 2.59 | 3.59 |

Example 2

Preparation of an Oral Suspension of Micronized Nitisinone Containing Methyl and Propyl Parabens as Preservatives A formulation according to the invention, as shown in Table II, was prepared according to standard procedures.

TABLE II

| Ingredient | Quantity (mg) | Function |
| --- | --- | --- |
| Nitisinone (micronized) | 4.0 | Active substance |
| Hydroxypropyl methylcellulose (HPMC) | 5.0 | Suspending agent |
| Glycerol | 500 | Sweetener |
| Polysorbate 80 | 0.135 | Surfactant |
| Methyl paraben | 1.4 | Preservatives |
| Propyl paraben | 0.14 | |
| Citric acid monohydrate | 8.98 | Buffer (pH 3.0) |
| Trisodium citrate dihydrate | 2.13 | |
| Water purified | q.s. to 1.00 ml | Solvent |

Example 3

Preparation of an Oral Suspension of Micronized Nitisinone Containing Sodium Benzoate as Preservative and Strawberry Aroma as Flavoring Agent A formulation according to the invention, as shown in Table III, was prepared according to standard procedures.

TABLE III

| Ingredient | Quantity (mg) | Function |
| --- | --- | --- |
| Nitisinone (micronized) | 4.0 | Active substance |
| Hydroxypropyl methylcellulose (HPMC) | 5.0 | Suspending agent |
| Glycerol | 500 | Sweetener |
| Polysorbate 80 | 0.135 | Surfactant |
| Sodium benzoate | 1.0 | Preservative |
| Strawberry aroma | 0.7 | Flavor agent |
| Citric acid monohydrate | 8.98 | Buffer (pH 3.0) |
| Trisodium citrate dihydrate | 2.13 | |
| Water purified | q.s. to 1.00 ml | Solvent |

Example 4

Preparation of a Nitisinone Solution for Comparison

A nitisinone solution as shown in Table IV was prepared according to standard procedures.

TABLE IV

| Ingredient | Quantity (mg) | Function |
|---|---|---|
| Nitisinone | 2.0 | Active substance |
| Methyl paraben | 1.8 | Preservatives |
| Propyl paraben | 0.2 | |
| $KH_2PO_4$ | 1.4 | Buffer (pH 6.8) |
| $Na_2HPO_4 \cdot 2H_2O$ | 2.9 | |
| NaOH (0.5M aqueous) | Adjust to pH 6.8 | |
| Water purified | q.s. to 1.00 ml | Solvent |

Example 5

Optimization of the Amounts of Preservatives by Microbial Challenge Studies According to the Europena Pharmacopoeia (pH Eur 5.1.3) and the United States Pharmacopoeia (USP <51>)

The results of different amounts of preservatives are shown in Tables V and VI, below.

TABLE V

Oral suspension of micronized nitisinone prepared according to Example 2 containing different amounts of methyl and propyl parabens as preservatives.

| | | Methyl paraben/Propyl paraben (mg/mL) | | | | | Limits | | |
|---|---|---|---|---|---|---|---|---|---|
| Microbe | Days | 0 | 1.0/0.1 | 1.4/0.14 | 1.7/0.17 | 2.0/0.2 | Ph Eur 5.1.3 | USP <51> | Units |
| S. aureus | Initial | 5.3-5.5 | 5.3-5.5 | 5.3-5.5 | 5.3-5.5 | 5.3-5.5 | — | — | log |
| | 14 | >3.5 | >3.5 | >3.5 | >3.3 | >3.5 | ≥3 | ≥1.0 | log red |
| | 28 | NI | NI | NI | NI | NI | NI | NI | log red |
| P. aeruginosa | Initial | 5.3-5.5 | 5.3-5.5 | 5.3-5.5 | 5.3-5.5 | 5.3-5.5 | — | — | log |
| | 14 | >3.3 | >3.5 | >3.5 | >3.4 | >3.5 | ≥3 | ≥1.0 | log red |
| | 28 | NI | NI | NI | NI | NI | NI | NI | log red |
| E. coli | Initial | 5.2-5.6 | 5.2-5.6 | 5.2-5.6 | 5.2-5.6 | 5.2-5.6 | — | — | log |
| | 14 | >3.7 | >3.6 | >3.6 | >3.2 | >3.6 | ≥3 | ≥1.0 | log red |
| | 28 | NI | NI | NI | NI | NI | NI | NI | log red |
| C. albicans | Initial | 5.3-5.6 | 5.3-5.6 | 5.3-5.6 | 5.3-5.6 | 5.3-5.6 | — | — | log |
| | 14 | 1.4 | >3.7 | >3.7 | >3.3 | >3.7 | ≥1 | NI | log red |
| | 28 | 2.2 | NI | NI | NI | NI | NI | NI | log red |
| A. brasiliensis | Initial | 5.5-5.6 | 5.5-5.6 | 5.5-5.6 | 5.5-5.6 | 5.5-5.6 | — | — | log |
| | 14 | 1.0 | 2.2 | 2.1 | 3.2 | >3.6 | ≥1 | NI | log red |
| | 28 | 1.0 | NI | 3.3 | 3.3 | NI | NI | NI | log red |

NI = No increase

TABLE VI

Oral suspension of micronized nitisinone prepared according to Example 3 containing different amounts of sodium benzoate as preservative.

| | | Sodium benzoate (mg/mL) | | | | Limits | | |
|---|---|---|---|---|---|---|---|---|
| Microbe | Days | 0.2 | 1.0 | 3.0 | 5.0 | Ph Eur 5.1.3 | USP <51> | Units |
| S. aureus | Initial | 5.3 | 5.3 | 5.3 | 5.3 | — | — | log |
| | 14 | 5 | 5 | 5 | 5 | ≥3 | ≥1 | log red |
| | 28 | NI | NI | NI | NI | NI | NI | log red |
| P. aeruginosa | Initial | 5.2 | 5.2 | 5.2 | 5.2 | — | — | log |
| | 14 | 5 | 5 | 5 | 5 | ≥3 | ≥1 | log red |
| | 28 | NI | NI | NI | NI | NI | NI | log red |
| E. coli | Initial | 5.4 | 5.4 | 5.4 | 5.4 | — | — | log |
| | 14 | 5 | 5 | 5 | 5 | ≥3 | ≥1 | log red |
| | 28 | NI | NI | NI | NI | NI | NI | log red |
| C. albicans | Initial | 5.8 | 5.8 | 5.8 | 5.8 | — | — | log |
| | 14 | 1.4 | 4.5 | 5 | 5 | ≥1 | NI | log red |
| | 28 | 4.1 | 5 | NI | NI | NI | NI | log red |
| A. brasiliensis | Initial | 5.6 | 5.6 | 5.6 | 5.6 | — | — | log |
| | 14 | 1 | 3.3 | 5 | 5 | ≥1 | NI | log red |
| | 28 | 1.3 | 5 | NI | NI | NI | NI | log red |

NI = No increase

The results show that all the above formulations according to the invention comply with the prescribed requirements for preservative effectiveness according to the European Pharmacopoeia (Ph Eur) and the U.S. Pharmacopeia (USP), including the preservative-free formulation indicating a self-preservative nature of the basic formulation.

Example 6

Stability Test

Samples from the oral suspension of micronized nitisinone prepared according to Example 2, as well as the nitisinone solution prepared according to Example 4, were put on stability at +5° C., +25° C. and +40° C., respectively, for 12 months. The concentrations of nitisinone and the degradation product 6-(trifluoromethyl)-3,4-dihydro-1H-xanthenene-1,9 (2H)-dione (oxotetrahydroxanthenone) were followed by HPLC with UV-detection. The results, shown in Tables VII to X, below, are expressed as percent of the nominal concentration of nitisinone (% of label claim).

TABLE VII

Oral suspension of micronized nitisinone
prepared according to Example 2.
Nitisinone (% of label claim)

| | Months | | | | | |
|---|---|---|---|---|---|---|
| Temperature | 0 | 1 | 2 | 3 | 6 | 12 |
| 5° C. | 99.9 | 104.2 | 101.7 | 105.0 | 102.9 | 104.8 |
| 25° C. | 99.9 | 105.6 | 98.6 | 104.0 | 101.8 | 103.7 |
| 40° C. | 99.9 | 105.6 | 102.0 | 102.7 | 101.0 | 100.1 |

TABLE VIII

Oral suspension of micronized nitisinone prepared according to Example 2
(nd = not detected).
Oxotetrahydroxanthenone (% of label claim)

| | Months | | | | | |
|---|---|---|---|---|---|---|
| Temperature | 0 | 1 | 2 | 3 | 6 | 12 |
| 5° C. | nd | nd | nd | nd | nd | nd |
| 25° C. | nd | nd | nd | nd | 0.02 | 0.02 |
| 40° C. | nd | nd | 0.07 | 0.15 | 0.28 | 0.54 |

TABLE IX

Nitisinone solution prepared according to Example 4.
Nitisinone (% of label claim)

| | Months | | | | | |
|---|---|---|---|---|---|---|
| Temperature | 0 | 1 | 2 | 3 | 6 | 12 |
| 5° C. | 96.6 | 99.8 | 95.3 | 100.4 | 99.7 | 99.3 |
| 25° C. | 96.6 | 100.9 | 96.0 | 100.2 | 98.0 | 95.9 |
| 40° C. | 96.6 | 98.3 | 96.3 | 93.6 | 86.5 | 74.4 |

TABLE X

Nitisinone solution prepared according to Example 4 (nd = not detected).
Oxotetrahydroxanthenone (% of label claim)

| | Months | | | | | |
|---|---|---|---|---|---|---|
| Temperature | 0 | 1 | 2 | 3 | 6 | 12 |
| 5° C. | nd | nd | nd | nd | 0.03 | 0.05 |
| 25° C. | nd | 0.01 | nd | 0.39 | 0.58 | 0.78 |
| 40° C. | nd | 0.07 | 1.86 | 2.05 | 1.63 | 1.38 |

The results show that the formulation according to the invention (Tables VII and VIII) is more stable than the solution for comparison (Tables IX and X) under all storage conditions. In the solution for comparison, the main degradation product, oxotetrahydroxanthenone, is further degraded to secondary degradation products. As a consequence it is not possible to achieve a mass balance between nitisinone and degradation products for the reference solution.

Example 7

Stability of Oxtetrahydroxanthenone

The stability study of the main degradation product in Example 6, oxotetrahydroxanthenone, is performed under similar conditions as described in Example 6. Samples of oxotetrahydroxanthenone (OTHX), 81 µg/ml in either citrate buffer pH 3.0 or phosphate buffer pH 6.8, were put on stability at +5° C., +25° C. and +37° C., respectively, for 6 months. The concentrations of OTHX and the secondary degradation products 1,3-cyclohexanedione (CHD) and 4-(trifluoromethyl)salicylic acid (TSA) were analyzed by LC-MS. The results, shown in Table XI, below, are expressed as percent of the initial concentration of OTHX. The mass balance expressed as the total recovery of CHD+OTHX+TSA compared to the initial concentration of OTHX were calculated from MmOTHX/(Mm CHD+MmTSA)×(CHDconc+TSAconc)+OTHXconc expressed in µg/ml where MmOTHX, MmCHD and MmTSA are the molecular masses corresponding to 282, 202 and 206 g/mol, respectively. The results for the mass balance, expressed as percent of initial concentration of OTHX, are shown in Table XII.

TABLE XI

Stability of solutions of oxotetrahydroxanthenone
prepared according to Example 7.

| | | Citrate buffer pH 3.0 Months | | | Phosphate buffer pH 6.8 Months | | |
|---|---|---|---|---|---|---|---|
| Component | Temp (° C.) | 1.8 | 3 | 6 | 1.8 | 3 | 6 |
| OTHX | 5 | 96.7 | 96.9 | 91.6 | 96.7 | 91.0 | 83.1 |
| | 25 | 96.7 | 102.7 | 92.3 | 74.8 | 63.2 | 44.8 |
| | 37 | 97.9 | 97.7 | 95.3 | 33.5 | 13.7 | 0.4 |
| CHD | 5 | 0.0 | 0.0 | 0.0 | 0.0 | 0.7 | 0.0 |
| | 25 | 0.0 | 0.0 | 0.0 | 7.7 | 9.7 | 25.2 |
| | 37 | 0.0 | 0.0 | 0.0 | 22.2 | 21.5 | 32.8 |
| TSA | 5 | 0.0 | 0.0 | 0.0 | 1.4 | 1.9 | 0.0 |
| | 25 | 0.0 | 0.0 | 0.0 | 13.0 | 20.2 | 36.4 |
| | 37 | 0.2 | 0.0 | 0.0 | 38.6 | 49.1 | 66.4 |

TABLE XII

Mass balance.

| | Citrate buffer pH 3.0 Months | | | Phosphate buffer pH 6.8 Months | | |
|---|---|---|---|---|---|---|
| Temp (° C.) | 1.8 | 3 | 6 | 1.8 | 3 | 6 |
| 5 | 96.7 | 96.9 | 91.6 | 97.9 | 93.3 | 83.1 |
| 25 | 96.7 | 102.7 | 92.3 | 93.2 | 89.8 | 99.4 |
| 37 | 98.1 | 97.7 | 95.3 | 87.4 | 76.3 | 88.5 |

The results show that the formulation according to the invention is surprisingly stable also with respect to the formation of secondary degradation products. The results, close to 100% for the mass balance, confirm that the LC-MS method is capable detecting and determining the majority of the secondary degradation products.

The invention claimed is:

1. A liquid pharmaceutical formulation suitable for oral administration, comprising
    (a) a suspension of 1 to 10 mg/ml of micronized 2-(2-nitro-4-trifluoromethylbenzoyl)-1,3-cyclohexanedione (nitisinone); and
    (b) a citric acid buffer, wherein the liquid pharmaceutical formulation has a pH in the range of 2.5 to 3.5.

2. The formulation according to claim 1 wherein the amount of nitisinone is 4 mg/ml.

3. The formulation according to claim 1, further comprising one or more pharmaceutically acceptable constituents selected from the group consisting of suspending agents, sweeteners, preservatives, surfactants, and flavoring agents.

4. The formulation according to claim 3 wherein the suspending agent is hydroxypropyl methylcellulose.

5. The formulation according to claim 4 wherein the suspending agent is hydroxypropyl methylcellulose in an amount of 1 to 20 mg/ml.

6. The formulation according to claim 3 wherein the sweetener is glycerol.

7. The formulation according to claim 6 wherein the sweetener is glycerol in an amount of 100 to 500 mg/ml.

8. The formulation according to claim 3 wherein the preservative is methyl paraben and/or propyl paraben.

9. The formulation according to claim 8 wherein the preservatives are methyl paraben in an amount of 1 to 2 mg/ml, and propyl paraben in an amount of 0.1 to 0.2 mg/ml.

10. The formulation according to claim 3 wherein the preservative is sodium benzoate in an amount of 0.2 to 5 mg/ml.

11. The formulation according to claim 3 wherein the surfactant is polysorbate 80.

12. The formulation according to claim 11 wherein the surfactant is polysorbate 80 in an amount of 0.1 to 20 mg/ml.

13. The formulation according to claim 1, comprising:
   (a) nitisinone (4 mg/ml);
   (b) citric acid monohydrate (9 mg/ml);
   (c) trisodium citrate dehydrate (2.1 mg/ml)
   (d) hydroxypropyl methylcellulose (5 mg/ml);
   (e) glycerol (500 mg/ml);
   (f) methyl paraben (1.4 mg/ml);
   (g) propyl paraben (0.14 mg/ml); and
   (h) polysorbate 80 (0.14 mg/ml).

14. The formulation according to claim 1, comprising:
   (a) nitisinone (4 mg/ml);
   (b) citric acid monohydrate (9 mg/ml);
   (c) trisodium citrate dehydrate (2.1 mg/ml)
   (d) hydroxypropyl methylcellulose (5 mg/ml);
   (e) glycerol (500 mg/ml);
   (f) sodium benzoate (1.0 mg/ml); and
   (g) polysorbate 80 (0.14 mg/ml).

15. The formulation according to claim 13, further comprising a flavoring agent.

16. A method of treating a medical condition in a subject, comprising administering to a subject in need of such treatment an effective amount of the formulation according to claim 1, wherein the medical condition is selected from the group consisting of tyrosinaemia, Parkinson's disease, depression, restless leg syndrome, and alkaptonuria.

17. The method according to claim 16, wherein the medical condition is hereditary tyrosinaemia type 1 (HT-1).

18. The method according to claim 17, wherein the medical condition is hereditary tyrosinaemia type 1 (HT-1) in a paediatric patient.

19. The formulation according to claim 14, further comprising a flavoring agent.

20. The formulation according to claim 1, wherein the liquid pharmaceutical formulation has a pH of 3.0.

21. The formulation according to claim 5, wherein the hydroxypropyl methylcellulose is in an amount of 5 mg/ml.

22. The formulation according to claim 7, wherein the glycerol is in an amount of 500 mg/ml.

23. The formulation according to claim 9, wherein the methyl paraben is present in an amount of 1.4 mg/ml, and the propyl paraben is present in an amount of 0.14 mg/ml.

24. The formulation according to claim 10, wherein the sodium benzoate is in an amount of 1 mg/ml.

25. The formulation according to claim 12, wherein the polysorbate 80 is an amount of 0.10 to 0.15 mg/ml.

* * * * *